(12) United States Patent
Archat et al.

(10) Patent No.: US 11,852,288 B2
(45) Date of Patent: Dec. 26, 2023

(54) CLAMPING DEVICE FOR FIXING A MEDICAL DEVICE ON A SUPPORT

(71) Applicant: Fresenius Vial SAS, Brézins (FR)

(72) Inventors: Damien Archat, Grenoble (FR); Mathieu Paoli, La Murette (FR); Philippe Traversaz, Saint Blaise du Buis (FR)

(73) Assignee: Fresenius Vial SAS, Brézins (FR)

( * ) Notice: Subject to any disclaimer, the term of this patent is extended or adjusted under 35 U.S.C. 154(b) by 73 days.

(21) Appl. No.: 17/620,606

(22) PCT Filed: Jun. 25, 2020

(86) PCT No.: PCT/EP2020/067766
§ 371 (c)(1),
(2) Date: Dec. 17, 2021

(87) PCT Pub. No.: WO2020/260429
PCT Pub. Date: Dec. 30, 2020

(65) Prior Publication Data
US 2022/0260202 A1    Aug. 18, 2022

(30) Foreign Application Priority Data
Jun. 26, 2019   (EP) ..................................... 19305855

(51) Int. Cl.
*F16M 13/02* (2006.01)
*F16B 2/06* (2006.01)
(Continued)

(52) U.S. Cl.
CPC ........... *F16M 13/022* (2013.01); *F16B 2/065* (2013.01); *A61B 90/57* (2016.02); *A61M 5/1415* (2013.01)

(58) Field of Classification Search
CPC .. F16M 13/022; F16M 2200/02; A61B 90/57; A61B 2090/571; A61M 5/1415; A61M 2209/082; F16B 2/065; F16B 2/12
See application file for complete search history.

(56) References Cited

U.S. PATENT DOCUMENTS 3,783,547 A    1/1974  Bystrom et al.
4,832,299 A *  5/1989  Gorton .................. F16M 11/10
                                                      403/92
(Continued)

FOREIGN PATENT DOCUMENTS

WO    WO-2015108844 A1 *  7/2015  ............. A61B 90/57
WO    WO2017/060166       4/2017

OTHER PUBLICATIONS

International Search Report and Written Opinion, counterpart International Appl. No. PCT/EP2020/067766 (dated Sep. 30, 2020) (9 pages).

*Primary Examiner* — Tan Le
(74) *Attorney, Agent, or Firm* — Cook Alex Ltd.

(57) ABSTRACT

A clamping device (2) for fixing a medical device (1) on a support (3) comprises a body (20) having a first jaw (200), an adjustment element (21) connected to a second jaw (210) and being adjustable with respect to the body (20) along a longitudinal axis (L) to establish a clamp connection with a support (3) in between the first jaw (200) and the second jaw (210), and a locking mechanism (22) for locking the adjustment element (21) with respect to the body (20) in a longitudinal position. Herein, the locking mechanism (22) comprises a coupling element (220) coupled to the adjustment element (21) and a locking element (224) coupled to the coupling element (220), wherein the adjustment element (21) is rotatable about the longitudinal axis (L) to thereby move the coupling element (220) and, by moving the coupling element (220), shift the locking element (224) with (Continued)

respect to the adjustment element (21) in order to engage the locking element (224) with the adjustment element (21) for locking the adjustment element (21) in its current longitudinal position or to disengage the locking element (224) from the adjustment element (21) in order to unlock the adjustment element (21) to allow a moving of the adjustment element (21) along the longitudinal axis (L).

14 Claims, 8 Drawing Sheets

(51) Int. Cl.
    *A61M 5/14*     (2006.01)
    *A61B 90/57*     (2016.01)

(56) References Cited

U.S. PATENT DOCUMENTS

| | | | |
|---|---|---|---|
| 4,844,397 A | | 7/1989 | Skakoon et al. |
| 5,174,533 A | | 12/1992 | Pryor et al. |
| 10,738,808 B2 | * | 8/2020 | Pryor .................. A61M 5/1415 |
| 11,639,767 B2 | * | 5/2023 | Johnson, Sr. .......... F16M 11/16 |
| | | | 248/176.1 |
| 2010/0252702 A1 | | 10/2010 | Spang, Jr. et al. |
| 2010/0258690 A1 | * | 10/2010 | Kleitsch .............. A61M 5/1417 |
| | | | 248/219.4 |
| 2018/0073528 A1 | * | 3/2018 | Pryor ....................... B25B 5/06 |

\* cited by examiner

CLAMPING DEVICE FOR FIXING A MEDICAL DEVICE ON A SUPPORT

The present application is a U.S. National Stage of PCT International Patent Application No. PCT/EP2020/067766, filed Jun. 25, 2020, which claims priority to EP Application No. 19305855.9, filed Jun. 26, 2019, both of which are hereby incorporated herein by reference.

The invention relates to a clamping device for fixing a medical device on a support according to the preamble of claim 1 and to a medical device.

A medical device, such as for example an infusion device for administering a medical fluid to a patient, such as a medication or a nutritional solution for enterally feeding a patient, may for example be arranged on a support such as a stand to place the medical device at the bedside of a patient in order to for example perform an infusion. For this, the medical device, if it is not placed on a rack for forming an organized stack of medical devices, may be fixed to a pole of the stand by using a clamping device for forming a clamping connection to the pole.

A clamping device of this kind comprises a body having a first jaw, an adjustment element connected to a second jaw and being adjustable with respect to the body along a longitudinal axis to establish a clamping connection with a support, such as pole, in between the first jaw and the second jaw, and a locking mechanism for locking the adjustment element with respect to the body in a longitudinal position.

Such clamping device generally shall form a secure and reliable connection to the support such that a medical device by means of the clamping device may be securely fastened to the support. At the same time, the clamping device shall be easy to handle, such that a clamping connection can be established in a fast and intuitive manner.

Herein, for forming the clamping connection, the adjustment element is adjusted with respect to the body of the clamping device, such that the second jaw arranged on the adjustment element is approached towards the first jaw formed on the body to clamp a support, such as a pole, in between the first jaw and the second jaw for forming a clamping connection. In this respect the handling of the adjustment element shall be easy and comfortable, hence avoiding that a user has to spend much effort to form the clamping connection.

It is an object of the instant invention to provide a clamping device for fixing a medical device on a support and a medical device having such clamping device, which allow to easily and comfortably form a reliable clamping connection to a support for fastening the medical device to the support.

This object is achieved by means of a clamping device comprising the features of claim 1.

Accordingly, the locking mechanism comprises a coupling element coupled to the adjustment element and a locking element coupled to the coupling element, wherein the adjustment element is rotatable about the longitudinal axis to thereby move the coupling element and, by moving the coupling element, shift the locking element with respect to the adjustment element in order to engage the locking element with the adjustment element for locking the adjustment element in its current longitudinal position or to disengage the locking element from the adjustment element in order to unlock the adjustment element to allow a moving of the adjustment element along the longitudinal axis.

The clamping device comprises an adjustment element which generally is movable along a longitudinal axis in order to approach the second jaw arranged on the adjustment element towards the first jaw formed on the body of the clamping device. Once the clamping connection is established, the adjustment element may be locked in its currently assumed longitudinal position with respect to the body by means of the locking mechanism. For this, the locking mechanism comprises a locking element, which may be brought into engagement with the adjustment element such that, in a locked position, the locking element holds the adjustment element in place and prevents a longitudinal movement of the adjustment element with respect to the body. The locking element can be disengaged from the adjustment element such that a longitudinal movement of the adjustment element becomes possible, hence allowing for a fast adjustment of the adjustment element for establishing the clamping connection with the support or for releasing the clamping device from the support.

The locking element is brought into engagement with the adjustment element or out of engagement from the adjustment element by rotating the adjustment element. Hence, a user may actuate the clamping device solely by acting onto the adjustment element, wherein, while the locking element is in its unlocked position, the adjustment element may be longitudinally moved with respect to the body in order to for example approach the second jaw arranged on the adjustment element towards the first jaw formed on the body for establishing the clamping connection and may then be rotated, once the clamping connection has been established, in order to lock the adjustment element in place such that the clamping connection is secured and the clamping device is securely fastened to the support.

Hence, an adjustment of the adjustment element becomes intuitive, easy and fast.

For longitudinally adjusting the adjustment element with respect to the body a user may simply move the adjustment element longitudinally with respect to the body while the locking element is in its unlocked position. To establish a locking of the adjustment element in a currently assumed longitudinal position, the user may rotate the adjustment element such that the locking element comes into engagement with the adjustment element. The locking herein may take place by rotating the adjustment element in a first rotation direction about the longitudinal axis for engaging the locking element with the adjustment element.

In contrast, for unlocking the adjustment element, the adjustment element may be rotated in a second rotation direction about the longitudinal axis opposite the first rotation direction to disengage the locking element from the adjustment element and to in this way unlock the adjustment element. Hence, for unlocking the adjustment element an opposite rotational movement (in comparison to the locking operation) is required, which comes intuitive to the user and allows, upon unlocking the adjustment element, to again freely slide the adjustment element along the longitudinal axis.

In one embodiment, the rotation of the adjustment element causes a movement of the coupling element, which causes the locking element to be shifted to engage with the adjustment element or to disengage from the adjustment element. The movement of the locking element herein may be substantially radial with respect to the longitudinal axis along which the adjustment element extends. The locking element hence is moved in a plane perpendicular to the longitudinal axis and, in a substantially radial direction, is brought into engagement with or out of engagement from the adjustment element.

In one embodiment, the adjustment element comprises an external thread for engaging with the locking element. The locking element, in turn, comprises a thread such that, when the locking element is engaged with the adjustment element, a thread connection is formed in between the adjustment element and the locking element such that a longitudinal movement of the adjustment element is blocked. The adjustment element herein may have the shape of a spindle extending along the longitudinal axis, the external thread extending substantially along the length of the adjustment element such that a locking of the adjustment element may be established over a substantial portion of the adjustment element, for example substantially over the entire length of the adjustment element.

In one embodiment, the coupling element is arranged on the adjustment element and is in friction connection with the adjustment element. The friction connection in between the coupling element and the adjustment element causes the coupling element to be carried along with the adjustment element when the adjustment element is rotated about the longitudinal axis. Hence, when the adjustment element is rotated, the coupling element is moved along about the longitudinal axis, which causes a shifting of the locking element due to the coupling of the coupling element to the locking element.

The friction connection herein may be such that a rotation of the adjustment element in the first rotation direction towards the locking position of the locking element causes the coupling element to be carried along until the locking element engages with the adjustment element and hence locks a longitudinal movement of the adjustment element. Once the locking element engages with the adjustment element, the coupling element may be held in place such that a further movement in the first direction of the adjustment element takes place under friction in between the clamping element and the adjustment element. In turn, when being rotated in the second rotation direction the adjustment element carries the coupling element along until the locking element has reached a fully disengaged position and hence the adjustment element is unlocked. A further rotation of the adjustment element in the second direction then takes place under friction in between the coupling element and the adjustment element, the coupling element being held in place and no longer being carried along with the adjustment element upon further rotation.

In one embodiment, the coupling element has the shape of a ring extending about the adjustment element. The ring is fitted on the adjustment element such that it is in frictional contact with the adjustment element. By the fitting of the ring on the adjustment element, the friction in between the adjustment element and the coupling element herein may be dimensioned such that the coupling element is reliably carried along when rotating the adjustment element in between the locked position and the unlocked position of the locking element.

In one embodiment, the locking element is pivotably connected to the coupling element about a pivot axis. Whereas the coupling element is for example arranged on the adjustment element, the locking element can be pivoted with respect to the coupling element, the pivot axis being radially displaced with respect to the longitudinal axis and hence being eccentric to the longitudinal axis. When moving the coupling element, the locking element is shifted with respect to the longitudinal axis by pivoting the locking element about the pivot axis in order to engage the locking element with the adjustment element or to disengage the locking element from the adjustment element.

In one embodiment, one or both of the coupling element and the locking element are axially fixed with respect to the body along the longitudinal axis. For example, the coupling element and the locking element may both be received within a cavity of the body, such that the coupling element of the locking element are axially held in place within the cavity, such that a longitudinal movement of the adjustment element along the longitudinal axis is not translated to the coupling element and the locking element, but the coupling element and the locking element remain in place when longitudinally moving the adjustment element with respect to the body.

In one embodiment, the adjustment element may be slidably movable with respect to the coupling element along the longitudinal axis when the locking element is disengaged from the adjustment element. When the locking mechanism is unlocked, hence, the adjustment element may be freely movable with respect to the coupling element such that, for establishing the clamping connection, the adjustment element with the second jaw arranged thereon may be approached towards the first jaw formed on the body or, for releasing the clamping connection, the adjustment element may be moved apart from the first jaw of the body.

In one embodiment, the locking element is operatively connected to a cam element arranged on the body. The cam element serves to guide the locking element with respect to the adjustment element when rotating the adjustment element about the longitudinal axis. The cam element is fixedly arranged on the body and is in operative connection with the locking element, such that the locking element upon a movement of the coupling element is caused to be shifted in between its unlocked position and its locked position.

For example, the cam element engages with a recess formed on the locking element. The recess may for example be bound by faces along which the cam element slides when the coupling element is moved when rotating the adjustment element. Dependent on the rotation direction of the adjustment element, the locking element hence is caused to be shifted radially inwards to engage with the adjustment element or radially outwards to disengage from the adjustment element.

In one embodiment, the coupling element is biased with respect to the body towards a rest position, the rest position corresponding to the unlocked position of the locking element (i.e., a position of the locking element in which the locking element is disengaged from the adjustment element). The spring element, in particular may serve to hold the coupling element and the locking element securely in the unlocked position. In the locked state, the spring element however generally may have a limited function in that the adjustment element is fastened in its locked position with respect to the coupling element and the locking element due to friction in between the different components.

A clamping device of this kind may be used for example on a medical device serving to administer a medical fluid to a patient, such as an infusion device in the shape of a volumetric (peristaltic) infusion pump or a syringe infusion pump. The medical device may however also be a rack serving to hold multiple infusion devices, the rack having to be fastened to a support of a stand for placing the rack at the bedside of a patient. Generally, a clamping device of the kind described herein may be used on any medical device which may need to be arranged on a support of a stand or the like, for example within a healthcare environment, such as a hospital.

The idea underlying the invention shall subsequently be described in more detail with respect to the embodiments shown in the figures. Herein.

Figure 1:
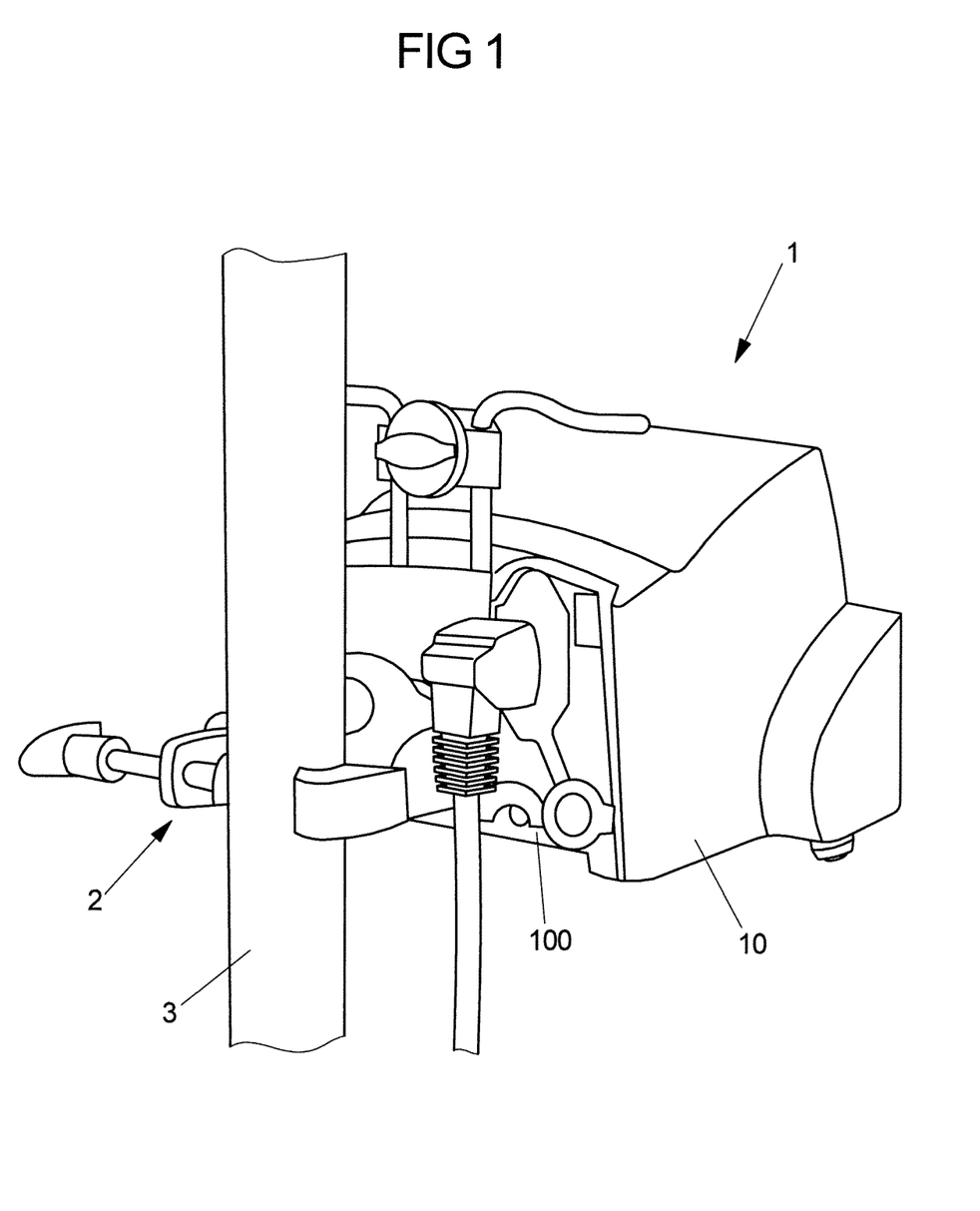
FIG. 1 shows a view of an embodiment of a medical device in the shape of an infusion device.

Referring to FIG. 1, a medical device 1 may have the shape of an infusion device serving to administer a medical fluid such as a medication or a nutritional solution to a patient.

The medical device 1 may have to be fastened to a stand having a support in the shape of a pole 3 such that the medical device 1 may be arranged for example at the bedside of a patient for performing an infusion operation.

The medical device 1, generally, comprises a housing 10 enclosing, for example, a pumping mechanism for performing a pumping action to deliver a medical fluid towards a patient. A clamping device 2 may be fixed to a backside 100 of the housing 10, the clamping device 2 being configured to establish a clamping connection to the pole 3 in order to fasten the medical device 1 to the pole 3.

Figure 2:
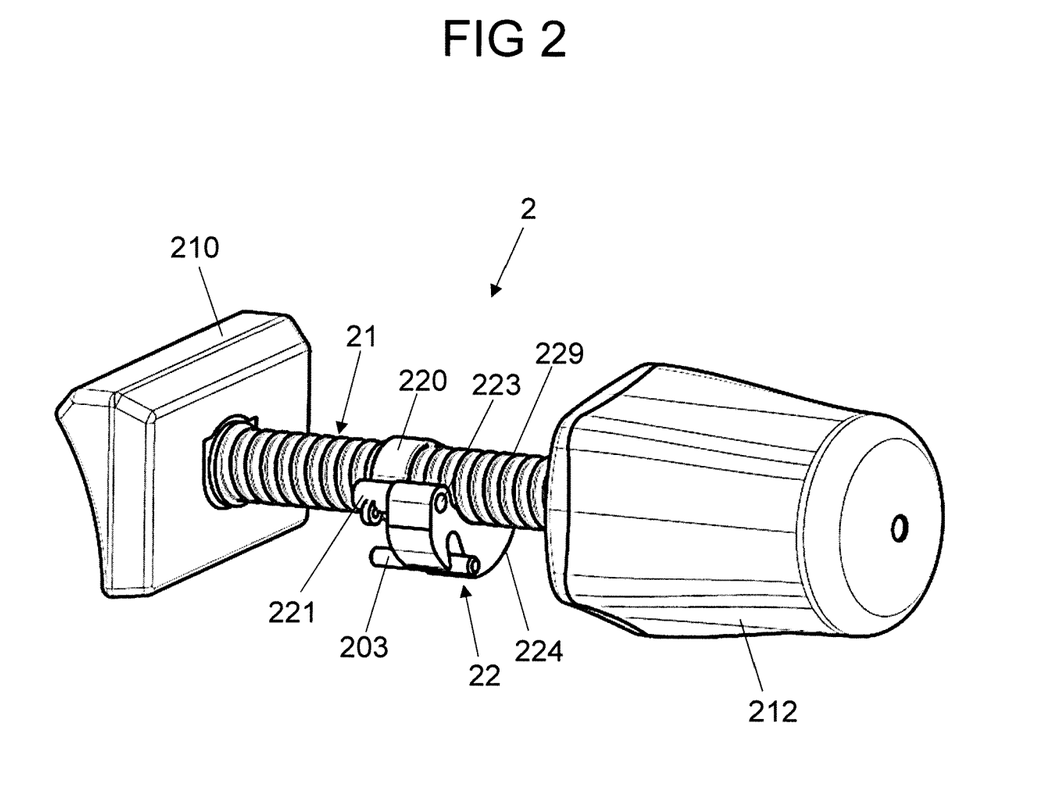
FIG. 2 shows an embodiment of a subgroup of a clamping device for establishing a clamping connection to a support.
Figure 3A:
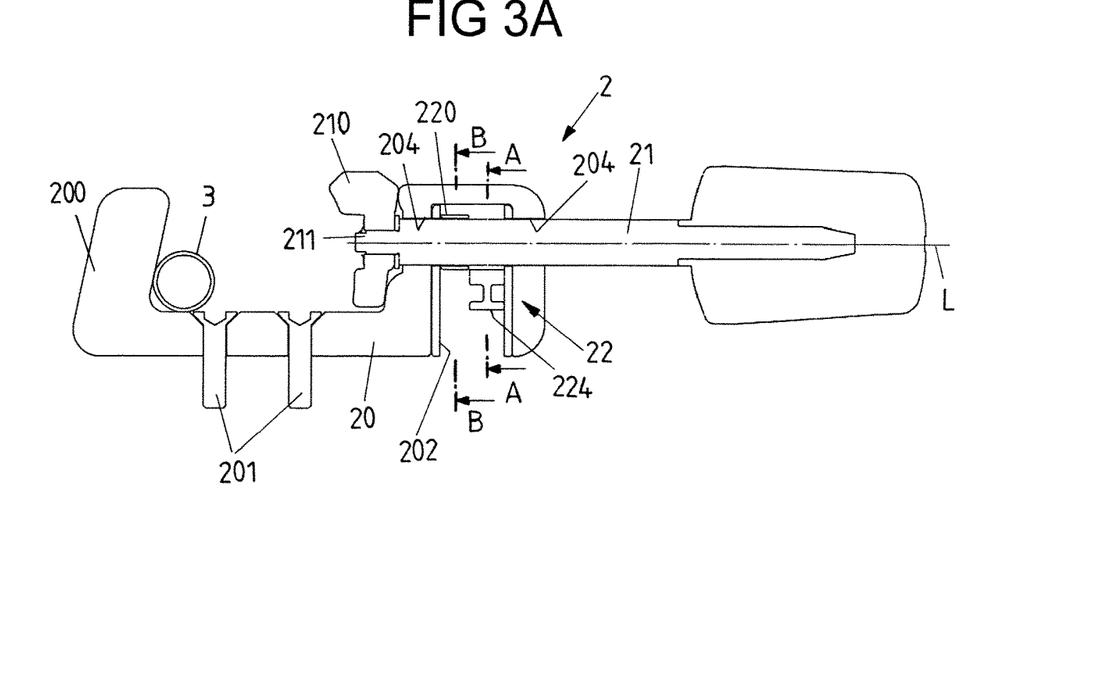
FIG. 3A shows a sectional view through an embodiment of a clamping device, in a released state, prior to establishing a clamping connection with a support.

Referring now to FIGS. 2 and 3A-3C, a clamping device 2, in one embodiment, comprises an adjustment element 21 arranged on a body 20 of the clamping device 2, the adjustment element 21 carrying a jaw 210 arranged on an end 211 of the adjustment element 21 for establishing a clamping connection to a pole 3 in between the jaw 210 and another jaw 200 formed on the body 20, as visible from FIG. 3A.

The body 20 may be fixed to the backside 100 of the housing 10 of an associated medical device 1 by means of fixing elements 201 in the shape of screws.

The clamping device 2 shall serve to establish a clamping connection in between the jaws 200, 210 and the pole 3 by approaching the jaw 210 arranged on the adjustment element 21 along a longitudinal axis L towards the jaw 200. Herein, the clamping device 2 shall allow for a fast establishing of the clamping connection and for a comfortable, intuitive handling by a user.

The adjustment element 21, in the embodiment of FIG. 2, has the shape of a spindle and comprises an external thread 229. The jaw 210 is rotatably arranged on the end 211 of the adjustment element 21. A head 212 at an end opposite the end 211 serves as a handle of the adjustment element 21, allowing a user to act onto the adjustment element 21 for moving the adjustment element 21 with respect to the body 20.

The adjustment element 21, as visible from FIG. 3A, is slidably arranged in bearing openings 204 formed on the body 20 of the clamping device 2. The adjustment element 21 hence may be moved along the longitudinal axis L through the bearing openings 204 to approach the jaw 210 towards the jaw 200 formed on the body 20, or to move the jaw 210 apart from the jaw 200.

The clamping device 2 comprises a locking mechanism 22, which substantially is formed by a coupling element 220 and a locking element 224 received in a cavity 202 of the body 20 such that the coupling element 220 and the locking element 224 are axially held in place with respect to the body 20.

As visible from FIG. 2, the coupling element 220 has the shape of a ring arranged on the adjustment element 21 and extending about the adjustment element 21, wherein the coupling element 220 is in frictional connection with the adjustment element 21, as shall be further explained below.

The locking element 224 has the shape of a so-called half nut, the locking element 224 being coupled to the coupling element 220 by means of a pivot axis 223, the pivot axis 223 allowing for a pivoting movement of the locking element 224 with respect to the coupling element 220.

At a side pointing radially inwards towards the adjustment element 21, the locking element 224, in one embodiment, is formed to have an internal thread suitable to engage with the external thread 229 of the adjustment element 21. By means of the locking element 224 a locking of the adjustment element 21 in a currently assumed longitudinal position may be established, wherein the locking element 224 may be unlocked from the adjustment element 21 in order to allow for a free sliding movement of the adjustment element 21 along the longitudinal axis L to approach the jaw 210 towards the jaw 200 or to move the jaw 210 apart from the jaw 200.

Figure 3B:
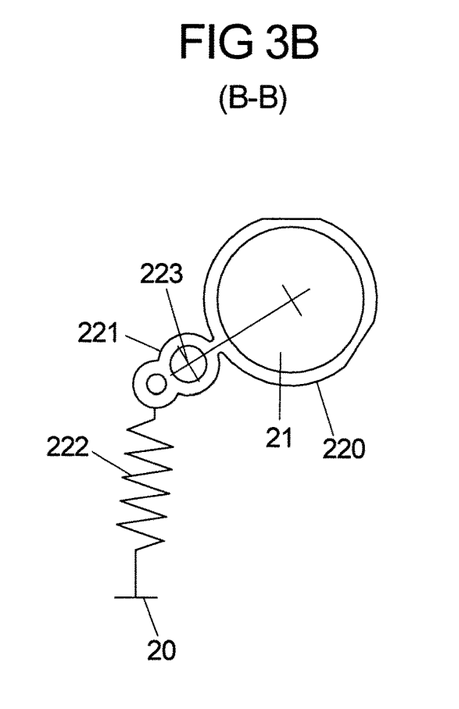
FIG. 3B shows a sectional view along line B-B according to FIG. 3A.

As is visible from FIG. 3B, the coupling element 220 comprises a bearing section 221 coupled to the pivot axis 223. A spring element 222 acts onto the bearing section 221 in order to bias the coupling element 220 towards the position shown in FIG. 3B.

Figure 3C:
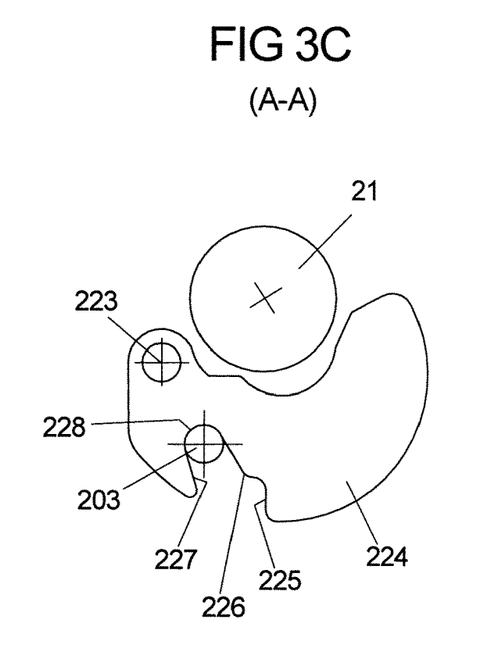
FIG. 3C shows a sectional view along line A-A according to FIG. 3A.

As visible from FIG. 3C, the locking element 224 comprises a recess 225 in which a cam element 203 fixedly arranged on the body 20 is received. The locking element 224 is coupled to the coupling element 220 by means of the pivot axis 223, wherein the locking element 224 is axially displaced with respect to the coupling element 220, as it is visible from FIG. 3A and FIG. 2. The cam element 203 serves to guide the locking element 224 to assume an unlocked position, corresponding to the position of FIG. 3C, or a locked position, depending on a movement of the coupling element 220.

The coupling element 220—having the shape of a ring and being fitted on the adjustment element 21 such that the coupling element 220 is frictionally connected to the adjustment element 21—serves to transfer a motion of the adjustment element 21 to the locking element 224 for shifting the locking element 224 with respect to the adjustment element 21 for locking or unlocking the locking mechanism 22. The frictional connection in between the coupling element 220 and the adjustment element 21 herein is such that the adjustment element 21 in principle is freely movable (under friction) with respect to the coupling element 220 along the longitudinal axis L, wherein—when the adjustment element 21 is longitudinally moved along the longitudinal axis L—the coupling element 220 remains axially in place within the cavity 202 of the body 20.

Figure 4A:
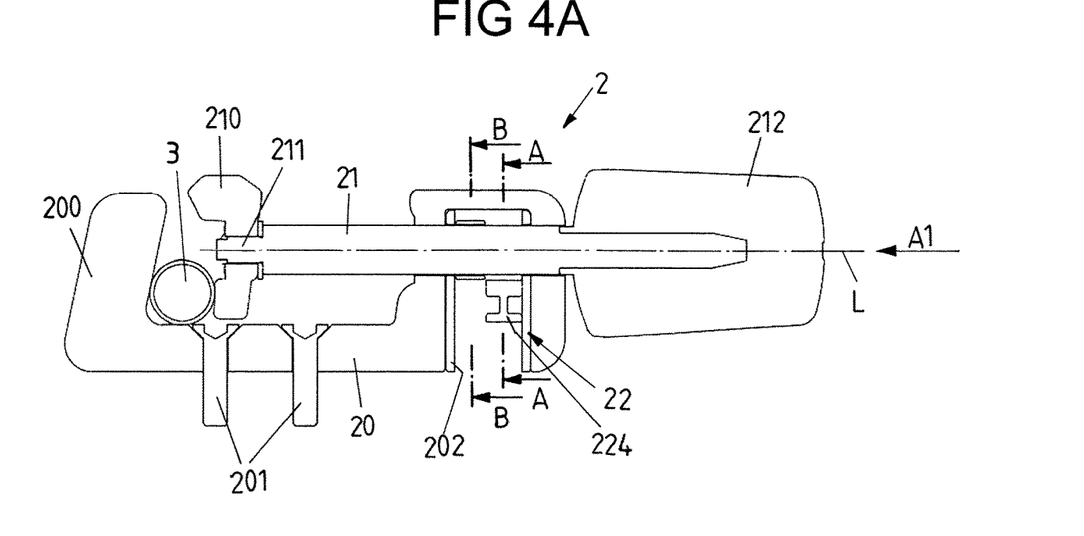
FIG. 4A shows the sectional view of FIG. 3A, after approaching an adjustment element with a jaw arranged thereon towards a support for establishing a clamping connection.
Figure 4B:
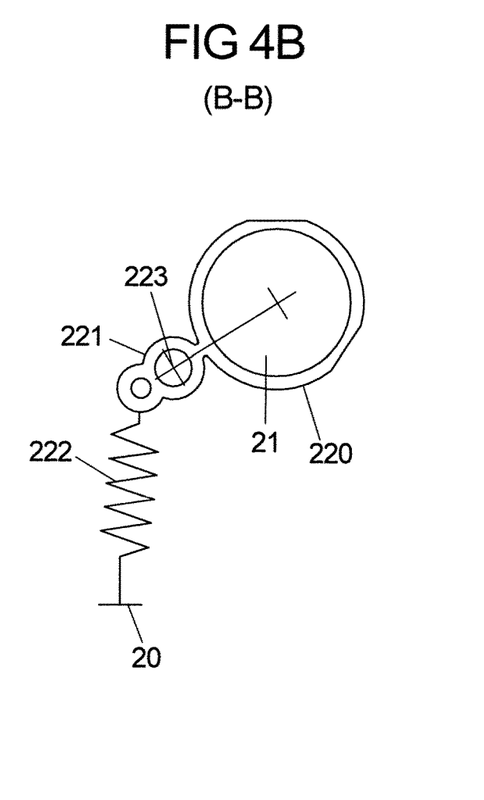
FIG. 4B shows a sectional view of the arrangement of FIG. 4A, along the line B-B.
Figure 4C:
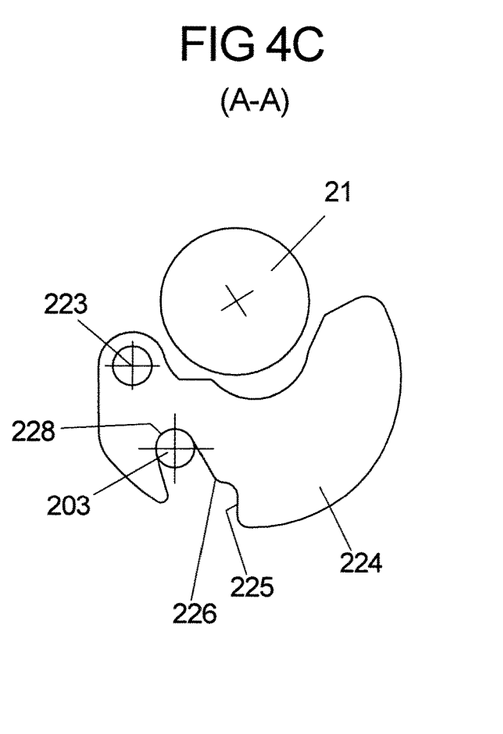
FIG. 4C shows a sectional view along line A-A according to FIG. 4A.

This allows, as shown in FIGS. 4A to 4C, to slidably move the adjustment element 21 in a longitudinal movement direction A1 to approach the jaw 210 towards the jaw 200 in order to establish a clamping connection of the jaws 200, 210 to a pole 3 received in between the jaws 200, 210.

As visible from FIG. 4C, during the sliding movement of the adjustment element 21 the locking element 224 is in its unlocked position. Hence, the locking element 224 is disengaged from the adjustment element 21 and hence does not block a longitudinal movement of the adjustment element 21.

As also visible from FIG. 4C, in the unlocked position the cam element 203 rests at an end 228 of the recess 225 formed on the locking element 224.

The spring element 222, as visible from FIG. 4B, herein serves to bias the coupling element 220 towards the unlocked position and holds the coupling element 220 in place in a stable fashion.

Figure 5A:
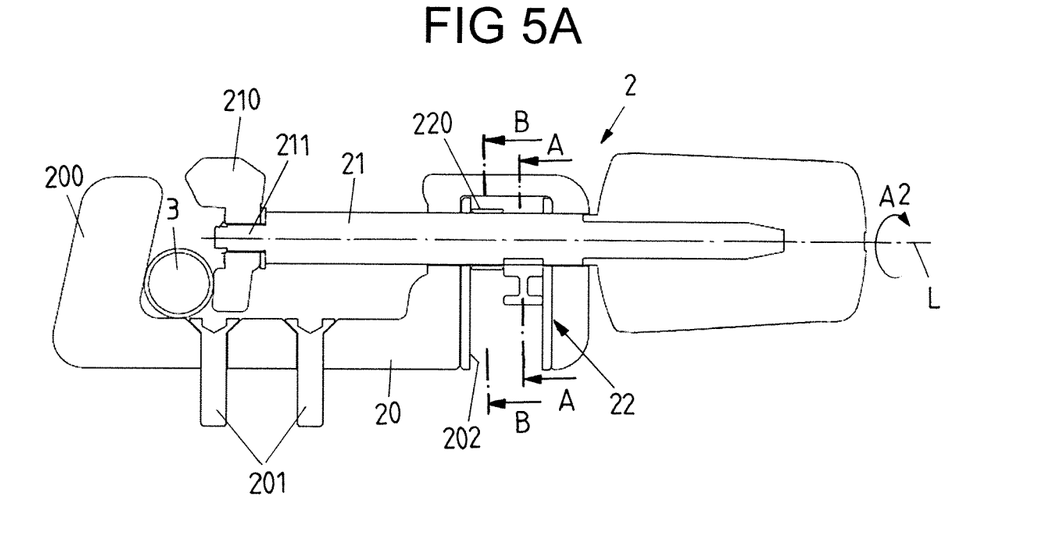
FIG. 5A shows the sectional view of FIG. 4A, after locking the adjustment element in its longitudinal position.
Figure 5B:
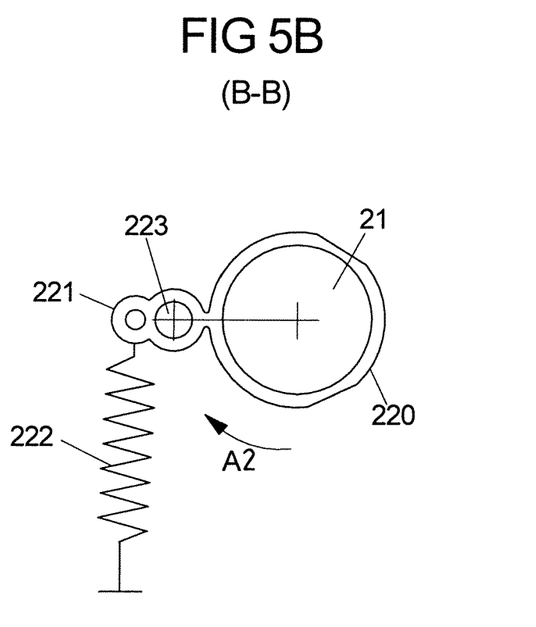
FIG. 5B shows a sectional view along line B-B according to FIG. 5A.
Figure 5C:
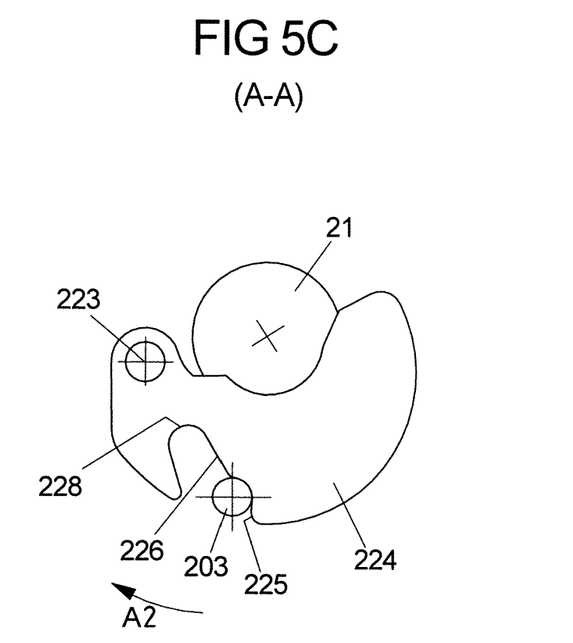
FIG. 5C shows a sectional view along line A-A according to FIG. 5A.
Figure 6A:
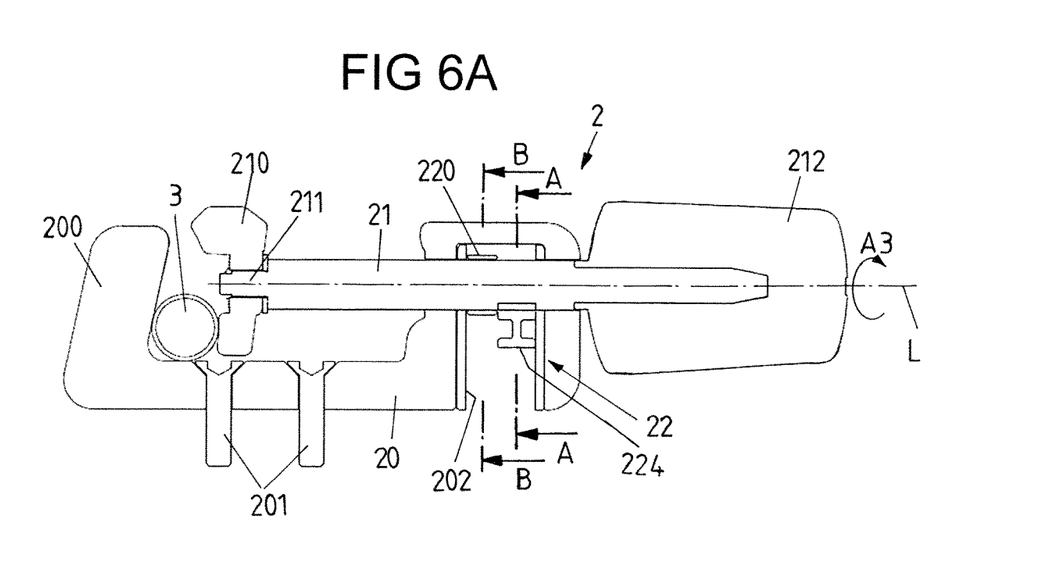
FIG. 6A shows the sectional view of FIG. 5A, when unlocking the adjustment element.
Figure 6B:
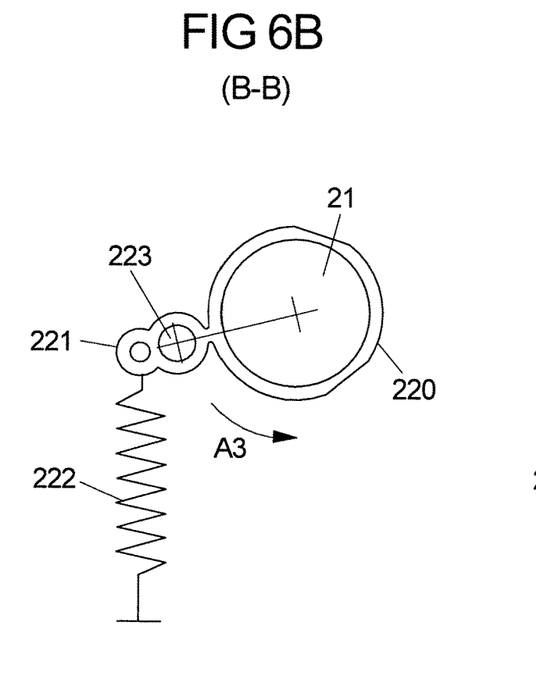
FIG. 6B shows a sectional view along line B-B according to FIG. 6A.
Figure 6C:
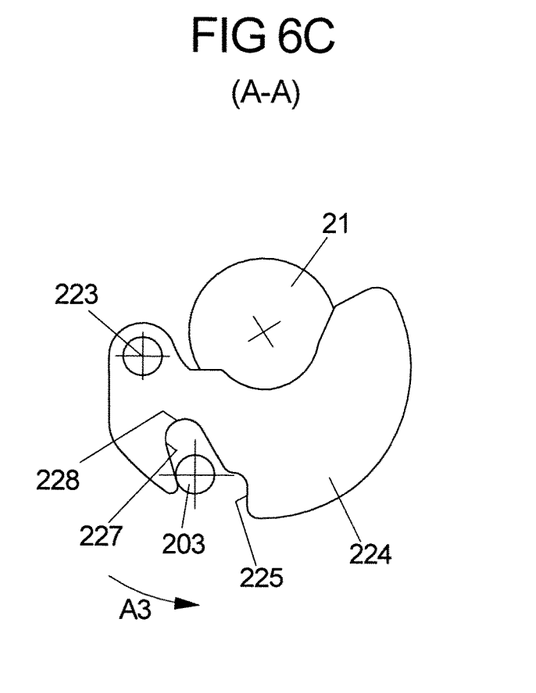
FIG. 6C shows a sectional view along line A-A according to FIG. 6A.
Figure 7A:
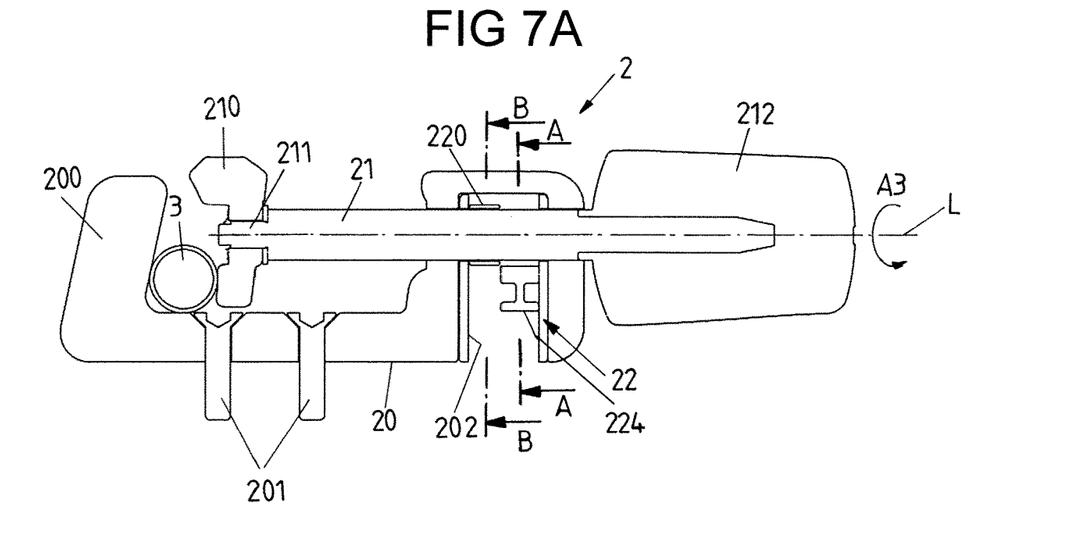
FIG. 7A shows the sectional view of FIG. 6A, after unlocking the adjustment element.
Figure 7B:
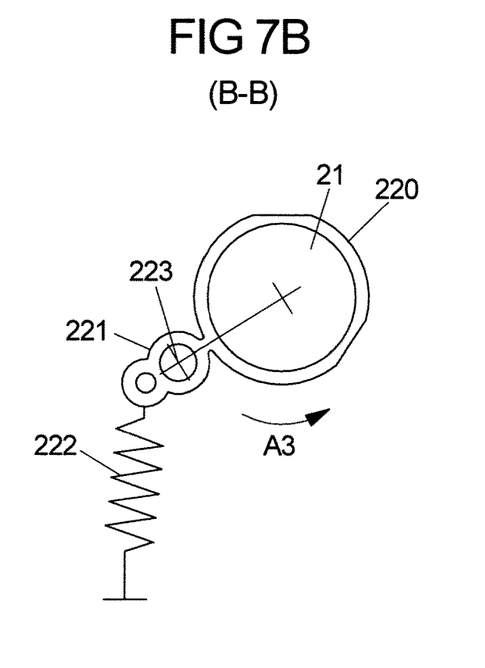
FIG. 7B shows a sectional view along line B-B according to FIG. 7A.
Figure 7C:
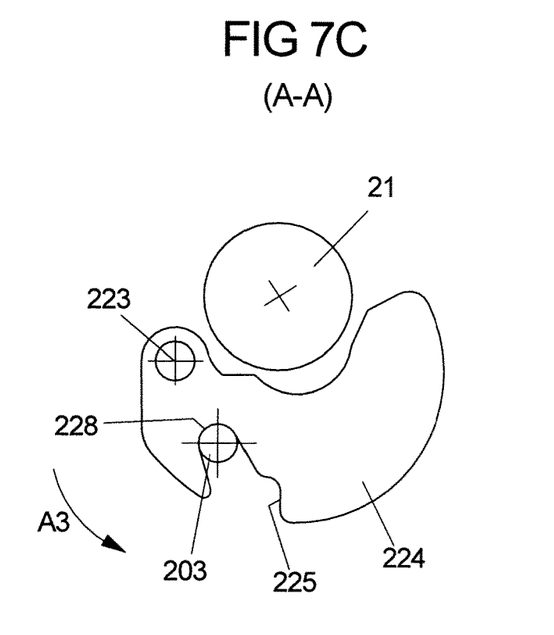
FIG. 7C shows a sectional view along line A-A according to FIG. 7A.

Once a desired position of the adjustment element 21 for establishing a clamping connection is reached, the adjustment element 21 may be rotated in a first rotation direction A2, as visible from FIGS. 5A to 5C, in order to cause a locking of the adjustment element 21 in its currently assumed longitudinal position. When rotating the adjustment element 21 in the first rotation direction A2 the coupling element 220 is moved along in the rotation direction A2, as visible from FIG. 5B, causing also the locking element 224 to be moved along. The moving of the locking element 224 is due to the coupling with the coupling element 220 via the pivot axis 223 and causes the cam element 203 to slide in the recess 225. The cam element 203 in this way acts onto the locking element 224 via a lock face 226 formed on the recess 225, as visible from FIG. 5C. The locking element 224 hence is shifted radially inwards with respect to the longitudinal axis L in order to engage with the adjustment element 21, such that the adjustment element 21 is locked in its current longitudinal position.

Hence, a user may lock the adjustment element 21 in place by acting onto the head 212 of the adjustment element 21. This may be carried out in a fast and intuitive manner, the longitudinal movement of the adjustment element 21 and the rotation of the adjustment element 21 being possible in a single and intuitive handling action by a user.

Once the locking element 224 is in threaded engagement with the adjustment element 21, a further movement of the adjustment element 21 in the rotation direction A2 does not cause the coupling element 220 to be further carried along. This may allow for a tightening of the clamping connection by screwing the adjustment element 21 further into clamping engagement with the pole 3.

For carrying the coupling element 220 along in the rotation direction A2, the frictional force in between the coupling element 220 and the adjustment element 21 is larger than the biasing force of the spring element 222.

In order to release the clamping connection, a user may act, as visible from FIGS. 6A to 6C and 7A to 7C, onto the head 212 and rotate the adjustment element 21 in a second rotation direction A3 opposite to the first rotation direction A2. In this way, the coupling element 220 again is carried along, but now in the opposite direction with respect to the locking operation, causing the locking element 224 also to be moved in the rotation direction A3, as visible from FIG. 6C. This causes the locking element 224 to be moved with respect to the cam element 203 (which is stationary on the body 20), such that the cam element 203 comes into abutment with a guide face 227 opposite the lock face 226 of the recess 225 and is guided towards the end 228 of the recess 225, as it is visible from the transition from FIG. 6C to FIG. 7C. This causes the locking element 224 to be shifted radially outwards, such that the locking element 224 comes out of engagement from the adjustment element 21. The adjustment element 21 hence is unlocked.

Figure 8A:
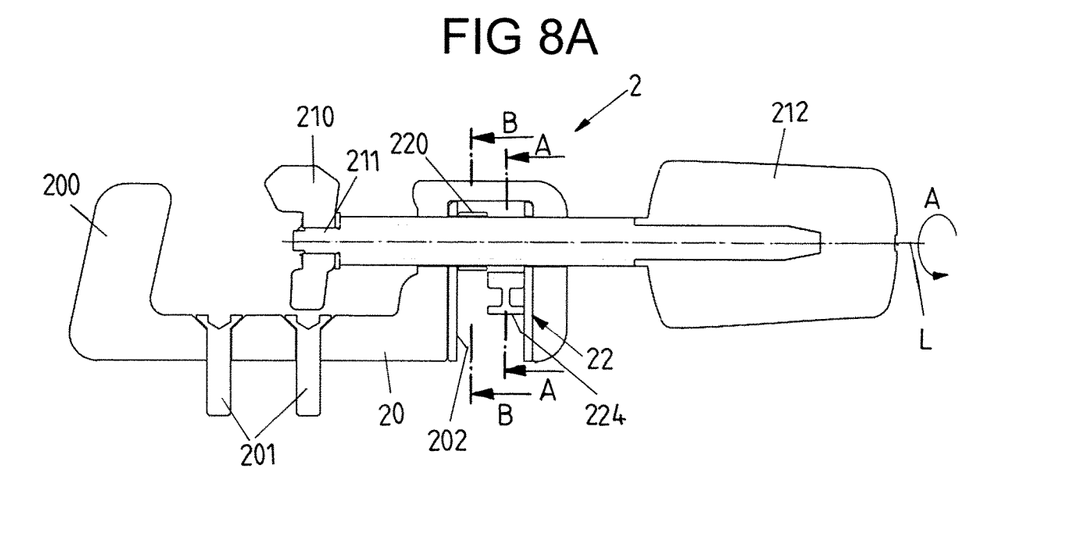
FIG. 8A shows the sectional view of FIG. 7A, after longitudinally moving the adjustment element.
Figure 8B:
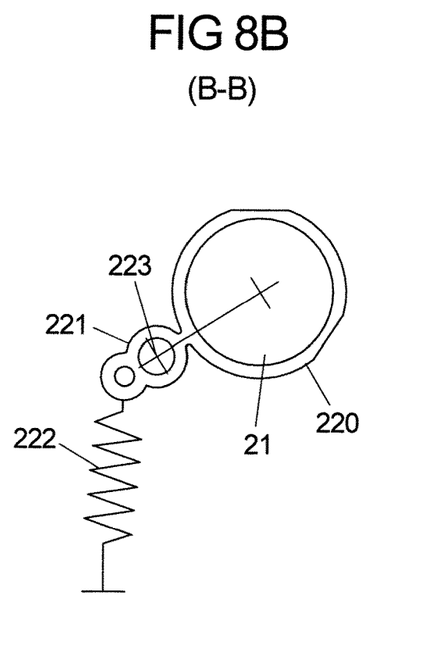
FIG. 8B shows a sectional view along line B-B according to FIG. 8A.
Figure 8C:
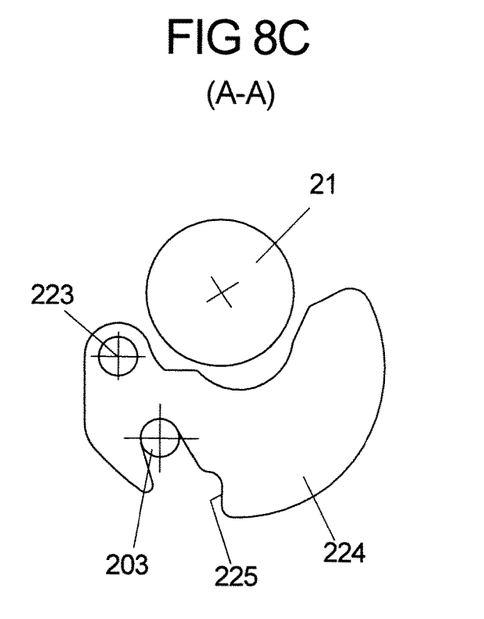
FIG. 8C shows a sectional view along line A-A according to FIG. 8A.

The adjustment element 21 hence may be longitudinally moved along the longitudinal axis L to for example move the jaws 200, 210 apart from one another, as this is visible from FIGS. 8A to 8C, in order to release a clamping connection.

Because a shifting motion of the locking element 224 may be exerted by acting onto the adjustment element 21 itself, the handling of the clamping device 2 both for establishing a clamping connection and for releasing a clamping connection is easy and intuitive, while allowing for a fast adjustment of the adjustment element.

In a locked position the adjustment element 21 herein is securely held in place, hence allowing for a fixed and reliable connection to a pole 3.

The idea underlying the invention is not limited to the embodiments described above, but may be implemented in an entirely different fashion.

A medical device may be a standalone infusion device or a rack for carrying multiple infusion devices. A medical device however may also be any other medical device which shall be fixed on a support such as a pole of a stand or another placement device in a healthcare environment.

LIST OF REFERENCE NUMERALS

1 Medical device
10 Housing
100 Back side
2 Clamping device
20 Body
200 Jaw
201 Fixing elements
202 Cavity
203 Cam element
204 Bearing opening
21 Adjustment element
210 Jaw
211 End
212 Head
22 Locking mechanism
220 Coupling element (ring element)
221 Bearing section
222 Spring element 223 Pivot axis
224 Lock element
225 Recess
226 Lock face
227 Guide face
228 End
229 External thread
3 Support
A1-A4 Movement
L Longitudinal axis

The invention claimed is:

1. A clamping device for fixing a medical device on a support, comprising:
   a body having a first jaw,
   an adjustment element connected to a second jaw and being adjustable with respect to the body along a longitudinal axis to establish a clamping connection with a support in between the first jaw and the second jaw, and
   a locking mechanism for locking the adjustment element with respect to the body in a longitudinal position, the locking mechanism comprising a coupling element coupled to the adjustment element and a locking element coupled to the coupling element,
   wherein the adjustment element is rotatable about the longitudinal axis to thereby move the coupling element, the coupling element attached to the locking element by a pivot to move and shift the locking element with respect to the adjustment element in order to engage the locking element with the adjustment element for locking the adjustment element in a current longitudinal position or to disengage the locking element from the adjustment element in order to unlock the adjustment element to allow a moving of the adjustment element along the longitudinal axis.

2. The clamping device according to claim 1, wherein the adjustment element is to be rotated in a first rotation direction for engaging the locking element with the adjustment element for locking the adjustment element in the current longitudinal position.

3. The clamping device according to claim 2, wherein the adjustment element is to be rotated in a second rotation direction opposite the first rotation direction for disengaging the locking element from the adjustment element in order to unlock the adjustment element to allow a moving of the adjustment element along the longitudinal axis.

4. The clamping device according to claim 1, wherein, by rotating the adjustment element, the locking element is shifted substantially radially with respect to the longitudinal axis to engage with or to disengage from the adjustment element.

5. The clamping device according to claim 1, wherein the adjustment element comprises an external thread for engaging with the locking element.

6. The clamping device according to claim 1, wherein the coupling element is arranged on the adjustment element and is in friction connection with the adjustment element, the friction connection being configured such that the coupling element is carried along when rotating the adjustment device about the longitudinal axis.

7. The clamping device according to claim 1, wherein the coupling element has the shape of a ring extending about the adjustment element.

8. The clamping device according to claim 1, wherein at least one of the coupling element and the locking element is axially fixed with respect to the body along the longitudinal axis.

9. The clamping device according to claim 1, wherein the coupling element and the locking element are received in a cavity of the body.

10. The clamping device according to claim 1, wherein the adjustment element is slidably movable with respect to the coupling element along the longitudinal axis when the locking element is disengaged from the adjustment element.

11. The clamping device according to claim 1, wherein the locking element is operatively connected to a cam element arranged on the body, the cam element being configured to guide the locking element with respect to the adjustment element when rotating the adjustment element about the longitudinal axis.

12. The clamping device according to claim 11, wherein the cam element engages with a recess formed on the locking element.

13. The clamping device according to claim 1, wherein the coupling element is biased with respect to the body towards a rest position, the rest position corresponding to a position of the locking element in which the locking element is disengaged from the adjustment element.

14. A medical device for administering a medical fluid to a patient, comprising a clamping device according to claim 1.

* * * * *